(12) United States Patent
Fanger et al.

(10) Patent No.: US 7,806,913 B2
(45) Date of Patent: Oct. 5, 2010

(54) MODULAR MULTI-LEVEL SPINE STABILIZATION SYSTEM AND METHOD

(75) Inventors: Jonathan P. Fanger, Fall River, MA (US); Charles M. Bartish, Jr., Providence, RI (US); Seungkyu Daniel Kwak, Grafton, MA (US); Matthew J. Andrie, South Easton, MA (US); Douglas R. LaSota, Saugus, MA (US)

(73) Assignee: DePuy Spine, Inc., Raynham, MA (US)

( * ) Notice: Subject to any disclaimer, the term of this patent is extended or adjusted under 35 U.S.C. 154(b) by 699 days.

(21) Appl. No.: 11/505,760

(22) Filed: Aug. 16, 2006

(65) Prior Publication Data

US 2008/0045951 A1 Feb. 21, 2008

(51) Int. Cl.
*A61B 17/70* (2006.01)
(52) U.S. Cl. .................. 606/260; 606/254; 606/257; 606/258; 606/259
(58) Field of Classification Search .................. 606/250, 606/251, 258–260; 403/292–298
See application file for complete search history.

(56) References Cited

U.S. PATENT DOCUMENTS

| | | | |
|---|---|---|---|
| 5,217,461 A | 6/1993 | Asher et al. | |
| 5,330,474 A | 7/1994 | Lin | |
| 5,387,213 A | 2/1995 | Breard et al. | |
| 5,403,314 A | 4/1995 | Currier | |
| 5,486,174 A | 1/1996 | Fournet-Fayard et al. | |
| 6,099,528 A | 8/2000 | Saurat | |
| 6,102,912 A | 8/2000 | Cazin et al. | |

(Continued)

FOREIGN PATENT DOCUMENTS

EP 0 669 109 8/1995

(Continued)

OTHER PUBLICATIONS

Betz et al., Comparison of Anterior and Posterior Instrumentation for Correction of Adolescent Thoracic Idiopathic Scoliosis, Spine, 1999, pp. 225-239, vol. 24(3), Lippincott Williams & Wilkins, Inc. (34 pages printed from internet web site http://ovidsp.tx.ovid.com).

(Continued)

*Primary Examiner*—Thomas C Barrett
*Assistant Examiner*—Andrew Yang
(74) *Attorney, Agent, or Firm*—Maginot, Moore & Beck

(57) ABSTRACT

A multi-level spine stabilization system comprises a plurality of securing members configured for attachment to a plurality of vertebrae. A plurality of adjustable rods segments extend between the plurality of securing members. The adjustable rod comprises a first rod segment that engages a second rod segment in an adjustable relationship. The length of the rod may be adjusted by moving the first rod segment relative to the second rod segment. For example, the first rod segment may be in a slideable relationship with the second rod segment such that sliding the first rod segment relative to the second rod segment results in a change in the length of the rod. In one embodiment, portions of both the first rod segment and the second rod segment are positioned within and secured to the securing member. Advantageously, the multi-level spine stabilization system described herein may be used to center dynamic portions of the rod between securing members.

6 Claims, 17 Drawing Sheets

U.S. PATENT DOCUMENTS

| | | | |
|---|---|---|---|
| 6,267,764 B1 | 7/2001 | Elberg | |
| 6,802,844 B2 * | 10/2004 | Ferree | 606/258 |
| 6,989,011 B2 | 1/2006 | Paul et al. | |
| 7,083,621 B2 * | 8/2006 | Shaolian et al. | 606/86 A |
| 7,556,639 B2 * | 7/2009 | Rothman et al. | 606/257 |
| 2003/0220643 A1 | 11/2003 | Ferree | |
| 2004/0049190 A1 | 3/2004 | Biedermann et al. | |
| 2004/0068258 A1 | 4/2004 | Schlapfer et al. | |
| 2004/0116927 A1 | 6/2004 | Graf | |
| 2004/0215191 A1 | 10/2004 | Kitchen | |
| 2004/0225289 A1 | 11/2004 | Biedermann et al. | |
| 2004/0236327 A1 | 11/2004 | Paul et al. | |
| 2005/0038432 A1 | 2/2005 | Shaolian et al. | |
| 2005/0065516 A1 | 3/2005 | Jahng et al. | |
| 2005/0085815 A1 | 4/2005 | Harms et al. | |
| 2005/0165396 A1 | 7/2005 | Fortin et al. | |
| 2005/0177157 A1 | 8/2005 | Jahng | |
| 2005/0182409 A1 | 8/2005 | Callahan et al. | |
| 2005/0203513 A1 | 9/2005 | Jahng et al. | |
| 2005/0203517 A1 | 9/2005 | Jahng et al. | |
| 2005/0203519 A1 | 9/2005 | Harms et al. | |
| 2005/0261686 A1 | 11/2005 | Paul | |
| 2005/0277922 A1 | 12/2005 | Trieu et al. | |
| 2005/0288672 A1 | 12/2005 | Ferree | |
| 2006/0009768 A1 | 1/2006 | Ritland | |
| 2006/0064090 A1 | 3/2006 | Park | |
| 2006/0106381 A1 | 5/2006 | Ferree et al. | |
| 2006/0149228 A1 | 7/2006 | Schlapfer et al. | |
| 2006/0229607 A1 | 10/2006 | Brumfield | |
| 2006/0264935 A1 | 11/2006 | White | |
| 2006/0264937 A1 | 11/2006 | White | |
| 2007/0049937 A1 | 3/2007 | Matthis et al. | |
| 2007/0129729 A1 | 6/2007 | Petit et al. | |
| 2007/0233064 A1 | 10/2007 | Holt | |
| 2008/0021469 A1 | 1/2008 | Holt | |
| 2008/0058812 A1 | 3/2008 | Zehnder | |

FOREIGN PATENT DOCUMENTS

| | | |
|---|---|---|
| EP | 1488751 | 12/2004 |
| EP | 1523949 | 4/2005 |
| EP | 1 579 816 | 9/2005 |
| WO | 9417745 | 8/1994 |
| WO | 9615729 | 5/1996 |
| WO | 0243603 | 6/2002 |
| WO | 2004024011 | 3/2004 |
| WO | 2004096066 | 11/2004 |
| WO | 2005030066 | 4/2005 |
| WO | 2005044117 | 5/2005 |
| WO | WO 2005/110257 | 11/2005 |
| WO | WO 2006/029373 | 3/2006 |

OTHER PUBLICATIONS

Poulin et al., Biomechanical modeling of instrumentation for the scoliotic spine using flexible elements: a feasibility study, Ann Chir. 1998, pp. 761-770, vol. 52, Issue 8, PubMed, (8 Pages printed from internet website http://www.ncbi.nlm.nih.gov including 7 page article and 1 page English language abstract).

\* cited by examiner

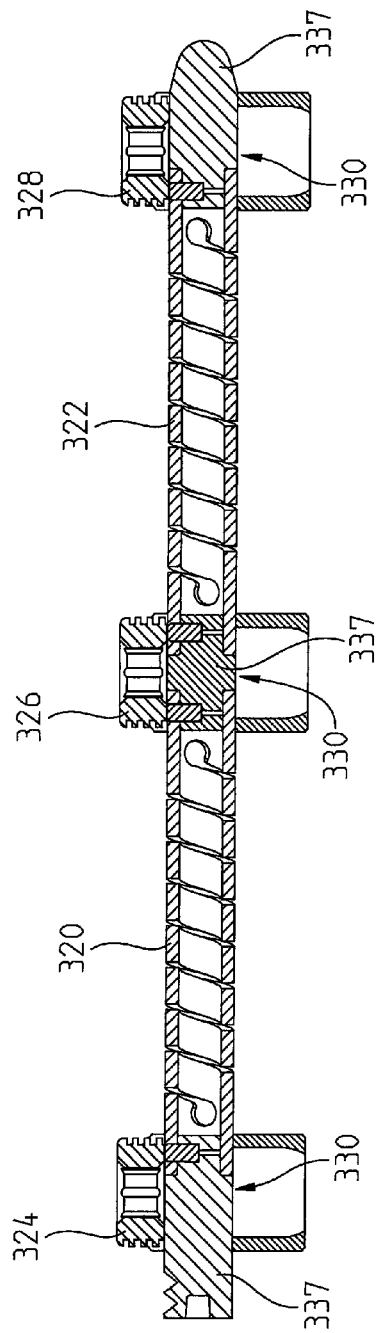
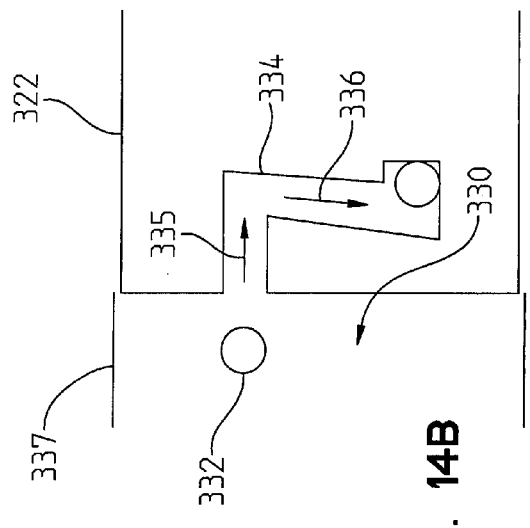
FIG. 14A
FIG. 14B

MODULAR MULTI-LEVEL SPINE STABILIZATION SYSTEM AND METHOD

FIELD

This application relates to the field of spinal stabilization devices. In particular, this application relates to posterior stabilization units configured for use with multiple segmental units of the spine.

BACKGROUND

Spinal surgeries are commonly used in the medical profession to treat spinal conditions that result when functional segmental units of the spine are moved out of proper position or otherwise damaged. Examples of procedures used to treat spinal conditions include disc replacement, laminectomy, and spinal fusion.

Following certain spinal procedures, such as spinal fusion, it is typically desirable to stabilize the spine by preventing movement between the vertebrae while the spine heals. This act of stabilizing the spine by holding bones in place during healing has greatly improved the success rate of spinal fusions and other procedures.

With spinal stabilization procedures, a combination of metal screws and rods creates a solid "brace" that holds the vertebrae in place. These devices are intended to stop movement from occurring between the vertebrae. These metal devices give more stability to the fusion site and allow the patient to be out of bed much sooner.

During the spinal stabilization procedure, pedicle screws are placed through the pedicle bone on the back of the spinal column. Each screw inserts through the pedicle and into the vertebral body, one on each side. The screws grab into the bone of the vertebral body, giving them a good solid hold on the vertebra. Once the screws are placed on the vertebra, they are attached to metal rods that connect all the screws together. When everything is bolted together and tightened, this creates a stiff metal frame that holds the vertebrae still so that healing can occur.

Posterior dynamic stabilization (PDS) generally refers to such a stabilization procedure where dynamic rods are positioned between the pedicle screws. These dynamic rods can generally bend, extend, compress, or otherwise deform in order to allow some limited movement between the pedicle screws. By allowing this limited movement between the pedicle screws and the associated segmental unit, less strain is placed on adjoining, non-stabilized functional segmental units during patient movements.

Depending upon the procedure performed, a multi-level stabilization system is often desired. These multi-level systems extend over a plurality of segmental units. Multi-level stabilization systems may also be PDS systems, incorporating dynamic flexible rods into the system. With such multi-level PDS systems, it is often important to properly center the dynamic portion of a rod between adjacent pedicle screws in order to properly provide limited movement between adjacent vertebrae. However, because of the difference in each unique patient size, and the difference in segmental unit sizes within a given patient, it is difficult to construct a multi-level PDS system where the dynamic portion of each rod is properly centered between adjacent pedicle screws.

Accordingly, it would be advantageous to provide an easy to use, modular PDS system that allows a surgeon to create a multi-level stabilization system including various dynamic segments. It would be of further advantage if such system could include various dynamic rods connected in series while requiring a minimal number of components capable of accommodating a large range of different patient sizes and anatomies. It would also be advantageous if the dynamic portions of the rods in such a multi-level stabilization system could be easily centered between pedicle screws.

SUMMARY

A multi-level spine stabilization system comprises a plurality of securing members configured for attachment to bone and a plurality of adjustable rods extending between the plurality of securing members. The adjustable rod comprises a first rod connected in series with a second rod segment in an adjustable relationship. The length of the rod may be adjusted by moving the first rod segment relative to the second rod segment. For example, the first rod segment may be in a slideable relationship with the second rod segment such that sliding the first rod segment relative to the second rod segment results in a change in the length of the rod.

Various embodiments of the adjustable rod segments are disclosed herein. In one embodiment, the first rod segment comprises a tube portion and the second segment of the rod comprises a junction portion configured to fit within the tube portion. The junction portion includes a channel configured to receive a set screw. The tube portion of the first segment includes a screw hole, and the tube portion of the first segment is secured to the junction portion of the second segment by tightening the set screw in the screw hole such that it engages the channel of the junction portion.

In another alternative embodiment, the first rod segment comprises a post member and the second rod segment comprises a channel. In this embodiment, the post member of the first segment is configured to slide within the channel of the second segment.

In yet another alternative embodiment, the first rod segment includes a first set of teeth and the second rod segment comprises a second set of teeth. The first set of teeth are configured to engage the second set of teeth as the first rod segment slides relative to the second rod segment.

In another alternative embodiment, the adjustable relationship between the first rod segment and the second rod segment is a threaded relationship. In this embodiment, the second member threadedly engages the first member and rotation of one member relative to the other results in a change in length of the rod.

Various means may be used to lock one rod segment relative to another rod segment. In one embodiment, the securing member configured for attachment to bone includes a cavity configured to receive the rod. Portions of the first rod segment and the second rod segment are both positioned within the securing member. The rod segments may be positioned in the cavity in an overlapping fashion, in an abutting fashion, or a non-contact fashion. After the rod segments are positioned in the cavity, the rod segments are locked to the securing member in order to fix the rod segments in place relative to each other. In one embodiment, a set screw is driven into the securing member to pin the rod segments in place within the securing member.

In one exemplary embodiment the rod segments are secured to the securing member using multiple ribs and grooves formed in the rod segments. In this embodiment, the securing member comprises a saddle including a first edge and a second edge. The grooves of the rod segments are configured to engage one of the edges of the saddle. After the rod segments are moved along the saddle to a desired location, the grooves of the rod segments are engaged with the saddle. A set screw is then used to pin the rod segments in place within the securing member.

In one alternative embodiment where the rod segments are fixed to the securing member, the first rod segment includes a first dovetail shaped tenon configured to fit within the cavity of the securing member. Likewise, the second rod segment also includes a second dovetail shaped tenon configured to fit within the cavity opposite the first tenon. After the tenons are placed within the cavity, a set screw may be used to pin the rod segments in place within the rod cavity.

Advantageously, the multi-level spine stabilization system described herein may be used to center dynamic portions of the rod between securing members. In this embodiment, the multi-level spine stabilization system comprises at least three securing members configured for attachment to three different vertebras. A multiple segment rod extends between the at least three securing members. The multiple segments of the rod are non-integral and may be separated from one another. Furthermore, because the length of the rod and/or related rod segments may be adjusted, a dynamic portion provided on a rod segment may be centrally positioned between two of the securing members.

The above described features and advantages, as well as others, will become more readily apparent to those of ordinary skill in the art by reference to the following detailed description and accompanying drawings.

BRIEF DESCRIPTION OF THE DRAWINGS

FIG. 14A shows a cross-sectional view of yet another alternative embodiment of a rod and bone anchor arrangement;

FIG. 14B shows a diagram of the connection between the rod segments of FIG. 14A;

DESCRIPTION

Figure 1:
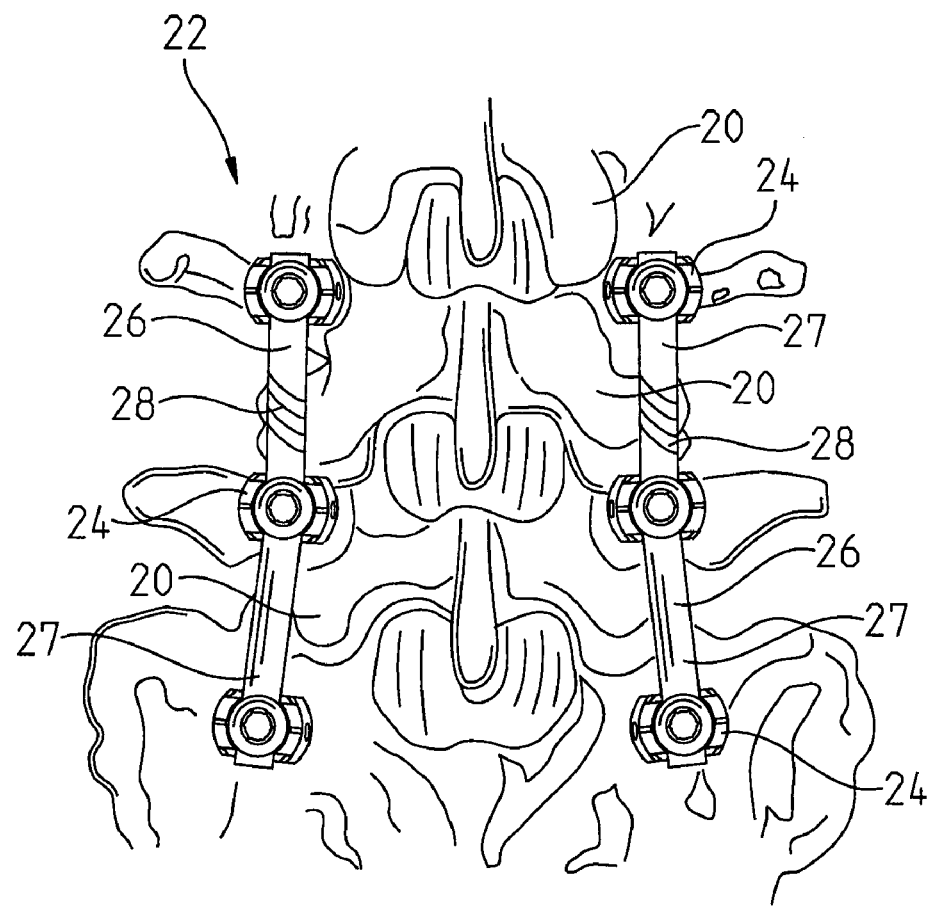
FIG. 1 shows a posterior view of a modular multi-level spine stabilization system connected to a plurality of vertebrae.
Figure 2:
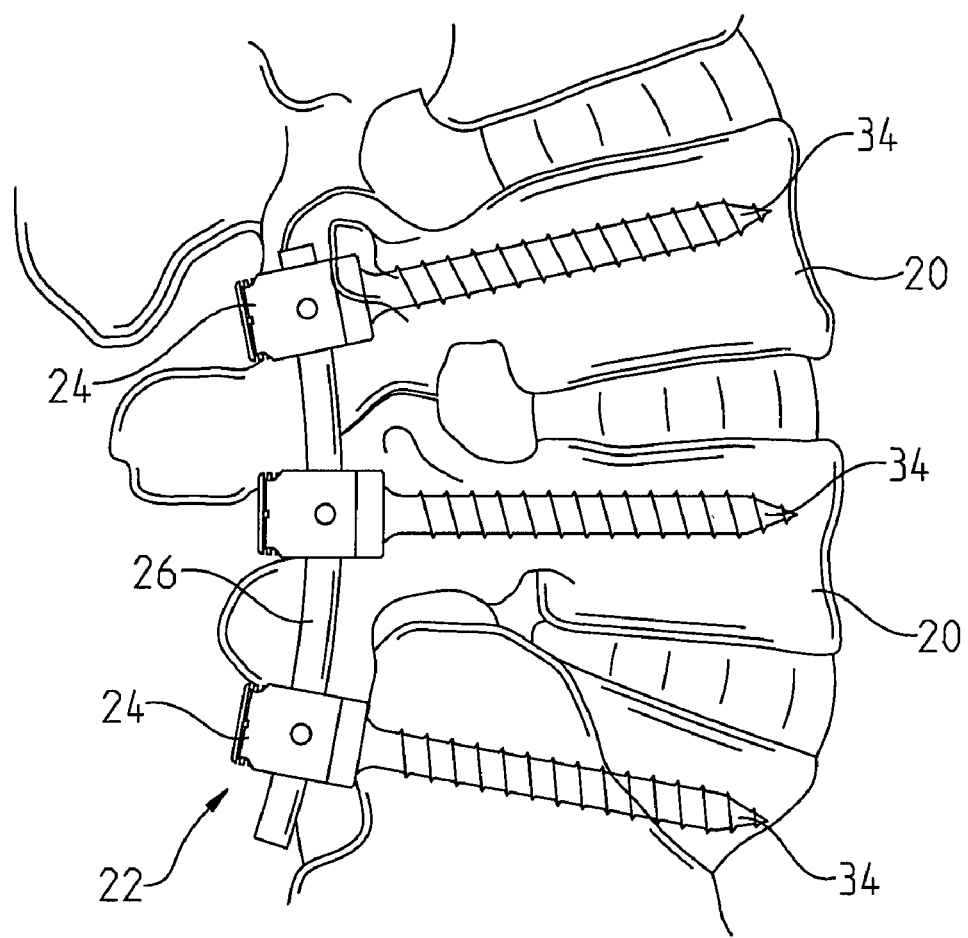
FIG. 2 shows a lateral view of the modular multi-level spine stabilization system of FIG. 1 with a see-through image of the vertebral bodies to show bone screws extending from securing members of the spine stabilization system.

With reference to FIGS. 1 and 2, a posterior dynamic stabilization (PDS) system 22 is shown arranged between several vertebrae 20 of a spine. The PDS system 22 comprises a plurality of securing members 24 configured for attachment to a bone. In the embodiment of FIG. 1, the securing members include bone anchors 24. A plurality of connecting structures in the form of rods 26 extend between the bone anchors 24. Each bone anchor 24 is fixed to the pedicle of one of the vertebrae 20 using a bone fixation device, such as a bone screw 34 designed to extend into a vertebra. Each rod 26 extends between a plurality of bone anchors 24. For example, a single rod 26 may extend from a first bone anchor fixed to an upper vertebra, to a second bone anchor fixed to an intermediate vertebra, and then to a third bone anchor fixed to a lower vertebra.

Figure 3:
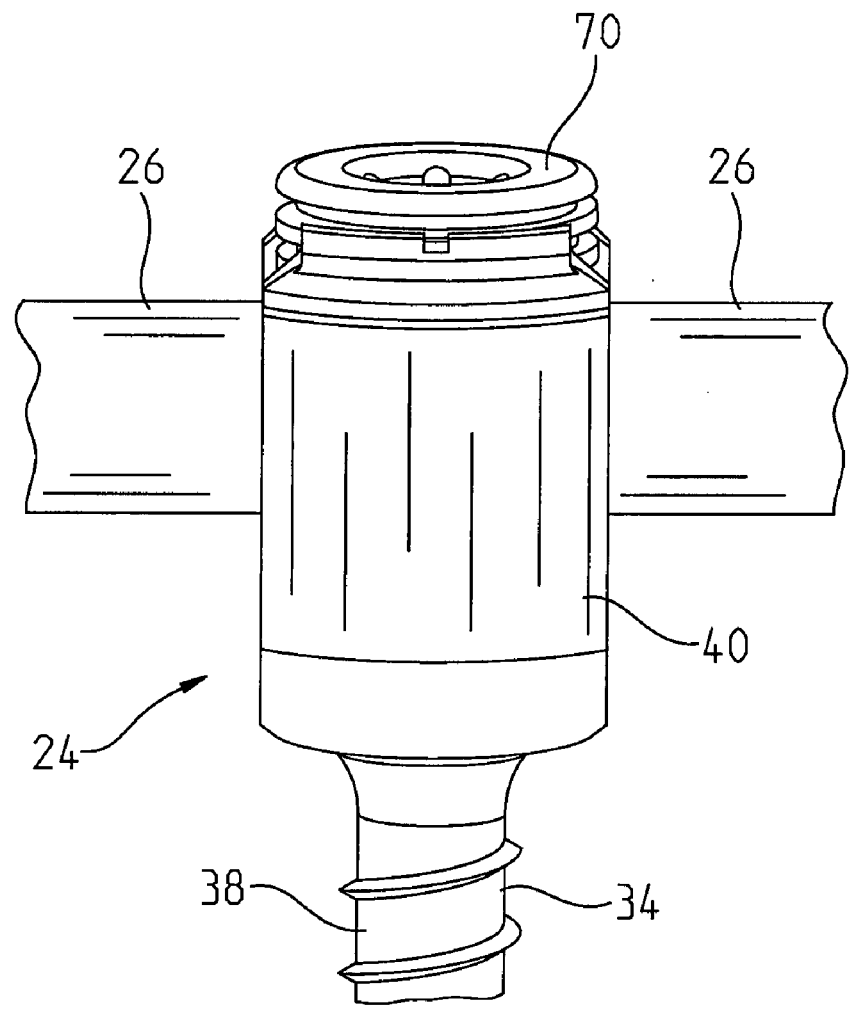
FIG. 3 shows a perspective view of a securing member of the spine stabilization system of FIG. 2 with a rod extending from the securing member.

Each bone anchor 24 is comprised titanium, stainless steel, or other appropriate biocompatible material. As generally shown in FIG. 3, each bone anchor 24 comprises a bone fixation member, such as a bone screw 34 (which may also be referred to herein as a "pedicle screw"). Although a bone screw is disclosed herein as the bone fixation member, one of skill in the art will recognize that other means may be used for securing the bone anchor to the bone. In addition to the fixation member, each bone anchor 24 also comprises a holding member 40 (which may also be referred to herein as a "head") such as a holding member configured to hold a screw and/or a rod. The bone screw 34 includes a screw shank configured to screw into the bone and secure the bone screw to the pedicile. The holding member may be rigidly or pivotably connected to the screw shank. The bone screw 34 may also include a screw head retained within the holding member 40. The holding member 40 is also configured to receive the rod 26. The rod 26 may be locked to the holding member 40 using a set screw 70.

While rods 26 are shown herein as the connecting structures 26 that extend between the between the bone anchors 24, other types of connecting structures are possible, as will be recognized by those of skill in the art. Furthermore, the term "rod" as used herein is intended to refer to any elongated bar-shaped member, whether having a rectangular, circular or other cross-sectional shape. With general reference to FIG. 4A, the rod 26 includes a plurality of non-integral rod segments 27 which may be connected together to form a complete rod 26. Each rod segment 27 includes two opposite ends 30, 32 that are connected to the bone anchors 24. Although not shown in FIG. 4A, connection members are provided on the rod segment ends 30, 32 to facilitate connection of each rod segment to another rod segment and/or connection of the rod segment ends 30, 32 to the bone anchors 24. Several examples of such connection members are described in further detail below. As will be understood with reference to the examples described below, the connection members may be provided as an integral component of a rod segment or provided as non-integral detachable components configured to engage rod segment ends and connect rod segments.

Figure 4A:
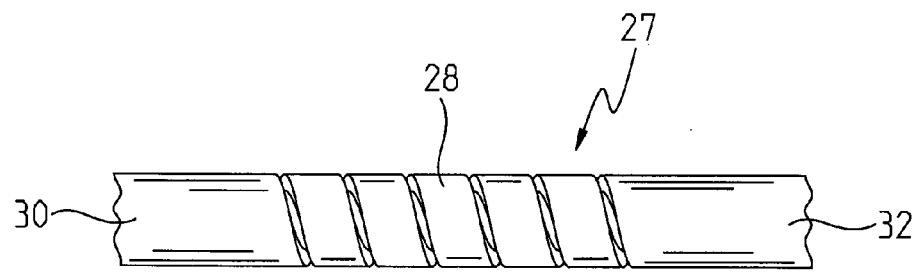
FIG. 4A shows an exemplary rod with a dynamic portion configured for use with the spine stabilization system of FIG. 1.
Figure 4B:
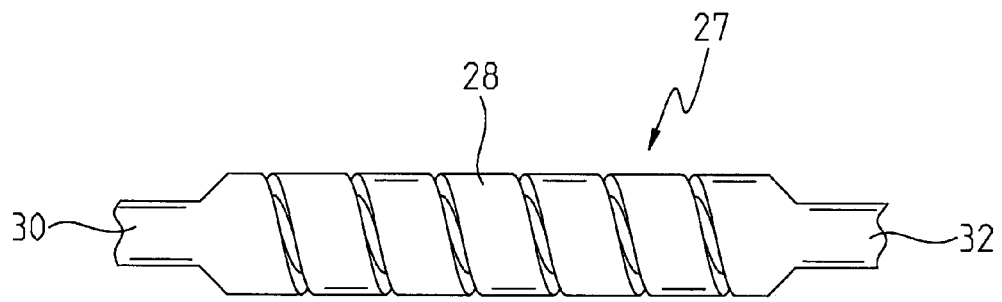
FIG. 4B shows another exemplary rod with a dynamic portion configured for use with the spine stabilization system of FIG. 1.

For some rod segments 27, such as the one shown in FIG. 4A, a flexible central portion 28 is disposed between the rod segment ends 30, 32. Although the rod segment 27 is generally rigid, the flexible central portion 28 of the rod segment allows for some limited flexibility in the rod segment. Therefore, when opposing forces are applied to the rod 26 at the rod segment ends 30, 32 which are fixed to the bone anchors 24, the dynamic central portion 28 flexes, allowing the rod 26 to bend. With this configuration, the PDS system generally stabilizes two adjacent vertebrae 20, while still allowing for some limited movement between the vertebrae 20. Although FIG. 4A shows the dynamic central portion 28 provided by a helical cut in a cylindrical rod segment, one of skill in the art will recognize that other dynamic central portions are possible. For example, as shown in FIG. 4B, the cylindrical rod segment 27 could be stepped with an increased diameter portion where the helical portion is located. Other examples of means for providing a dynamic central portion 28 in a rod segment 27 include the following: two piece rods with an internal central core of varying stiffness, constructing the rod segment from materials of varying stiffness, varying the diameter of the rod to provide varying stiffness, covering the central core with a polymer jacket to reduce friction between the central portion and the internal central core, as well as numerous other means as will be recognized by those of skill in the art.

Figure 5:
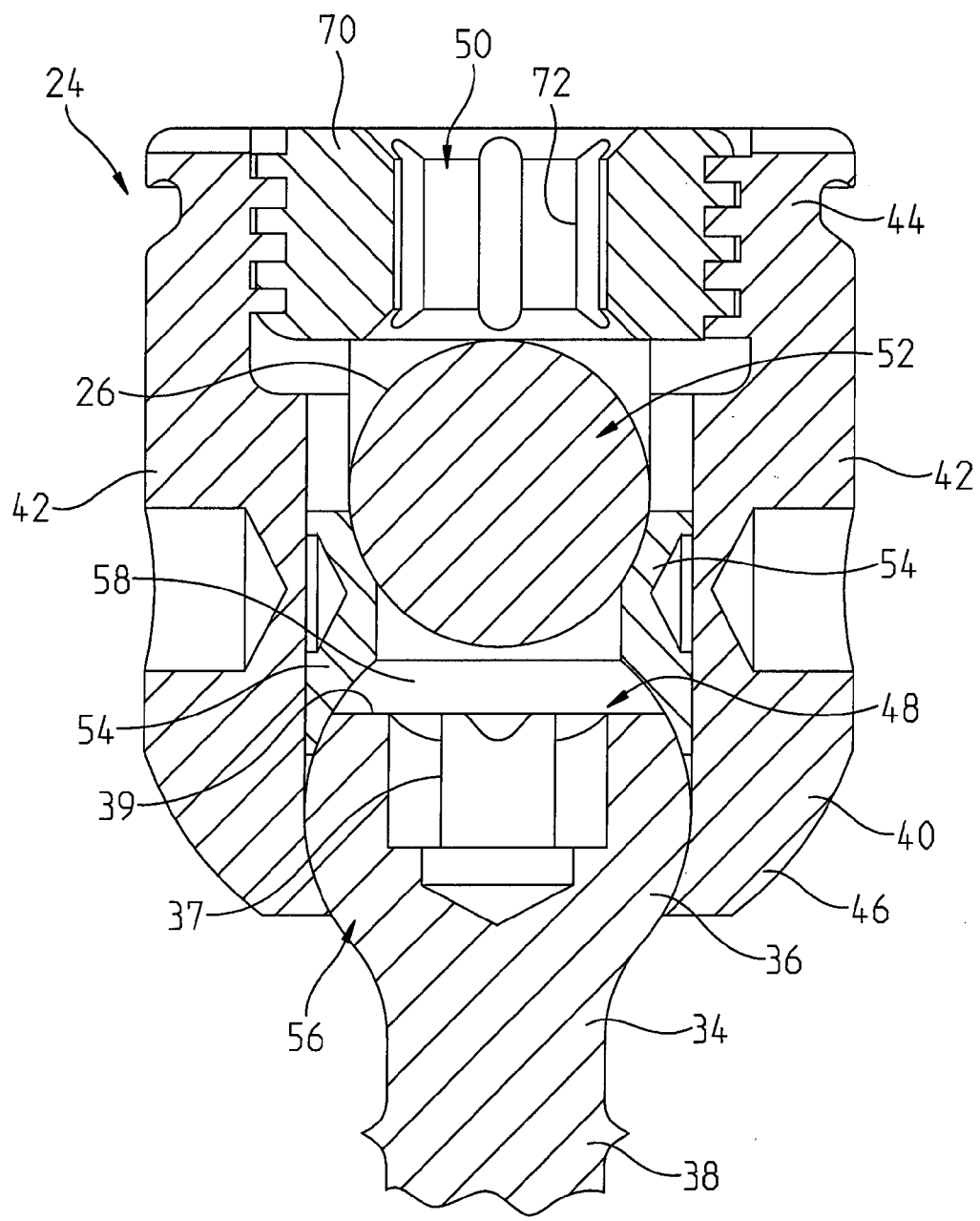
FIG. 5 shows a cross-sectional view of a bone anchor of the spine stabilization system of FIG. 1.

With reference now to FIG. 5, one embodiment of a bone anchor assembly 24 is shown. The bone anchor assembly 24 comprises a bone screw 34 retained within a screw holding member 40. The bone screw 34 comprises a screw head 36 and a screw shank 38. The screw head 36 is generally spherical in shape with a flat top 39. A slot 37 is formed in the top of the screw head 36. The slot 37 is configured to receive the tip of a screwdriver that may be used to drive the screw 34 into the bone. The screw shank 38 extends from the screw head 36. The screw shank 38 is threaded to facilitate driving the screw into the pedicle and vertebral body.

The holding member 40 is a generally cup-shaped structure configured to hold both the screw 34 and the rod 26. The holding member comprises substantially cylindrical sidewalls 42 formed between a superior end 44 and an inferior end 46. A bone screw cavity 48 is formed within the sidewalls 42 near the inferior end 46. A set screw cavity 50 is formed within the sidewalls 42 near the superior end 44. A rod cavity and passage 52 is formed in the holding member between the set screw cavity 50 and the bone screw cavity 48.

The set screw cavity 50 is designed and dimensioned to receive a set screw 70. Accordingly, the cylindrical sidewalls 42 of the holding member are threaded at the superior end 44. These threads are configured to engage the threads on the set screw 70. The set screw includes a slot 72 in the top that is adapted to receive the tip of a screwdriver, thus allowing the set screw 70 to be driven into the set screw cavity 50.

The rod passage 52 is provided directly below the set screw cavity 50. The rod passage 52 is designed and dimensioned to receive one or more of the rod segments 26 of the PDS system 22. In particular, the rod passage 52 is designed to receive at least one end 30, 32 of a rod segment 27. In the embodiment of FIG. 5, the rod is loaded into the rod passage from the top of the holding member by passing the rod first through the set screw cavity 50 and then into the rod passage 52. After the rod 26 is positioned in the rod passage 52, a set screw 70 is driven into the set screw cavity 50 until the set screw contacts the rod 26. When the set screw 70 it tightened, it locks the rod 26 in place within the holding member 40. Although the embodiment of FIG. 5 has been described with a set screw, one of skill in the art will recognize that other appropriate locking features may be used to hold the rod in place.

With continued reference to FIG. 5, the bone screw cavity 48 is designed and dimensioned to retain the screw head 36 of the bone screw 34, with the shank 38 of the bone screw extending from the holding member 40. An opening 56 is formed in the inferior end 46 of the holding member 40. The diameter of the opening 56 is smaller than the diameter of the screw head 36, but it is large enough to allow the screw shank 38 to pass through the opening 56.

A bearing member 54 is positioned within the bone screw cavity 48 along with the screw head 36. The bearing member 54 includes an inner bearing surface that generally conforms to the spherical shape of the screw head 36 while still providing room for the screw head 36 to rotate and pivot within the bearing member 54. The outer bearing surface is designed and dimensioned to engage the interior portion of the cylindrical sidewalls 42 of the holding member. While the embodiment of FIG. 5 shows that the screw 34 may pivot within the holding member 40, in other embodiments, the screw head 36 may be locked within the holding member 40.

In the embodiment of FIG. 5, the bearing member 54 extends into the rod cavity 52 and provides a bearing surface for the rod 26. This bearing surface conforms to the shape of the rod 26, which is generally cylindrical in the disclosed embodiment. When the rod 26 is forced downward by the set screw 70, the rod 26 compresses the bearing member 54 and locks the bearing member 54 in place within the holding member 40.

Adjustable Rod Segments

Figure 6A:
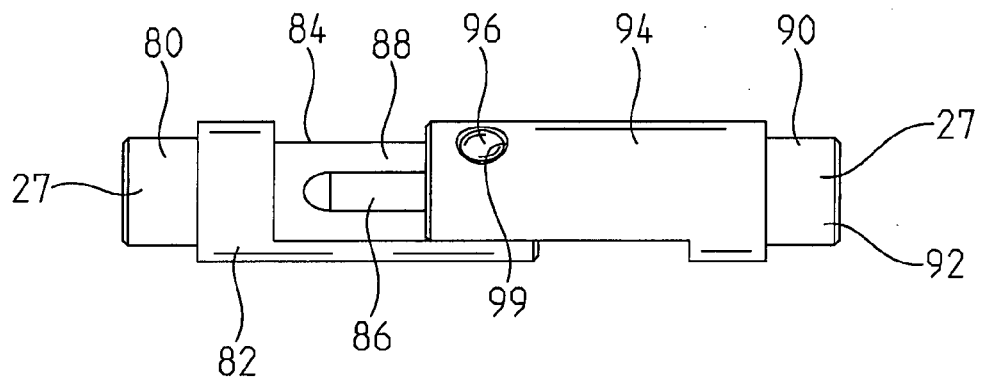
FIG. 6A shows a perspective view of an exemplary embodiment of an adjustable rod configured for use with the spine stabilization system of FIG. 1.
Figure 6B:
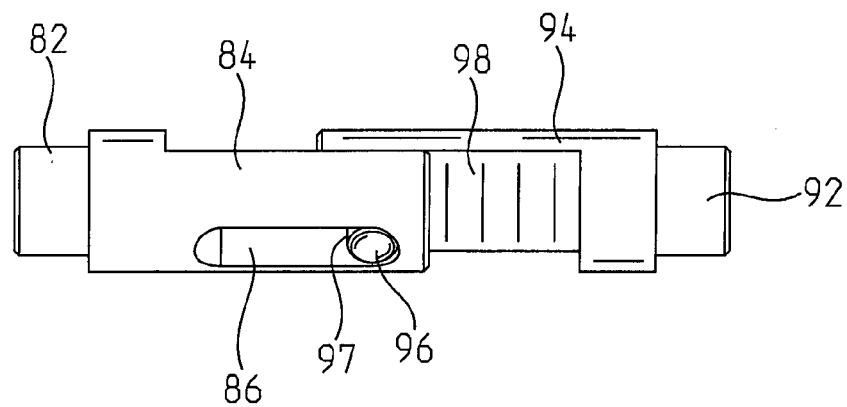
FIG. 6B shows a perspective view of an alternative embodiment of the adjustable rod of FIG. 6A.

With reference now to FIGS. 6A and 6B, two complimentary rod segments 27 are shown configured for use in a multi-level PDS system 22. The rod segments 27 include a first rod segment 80 and a second rod segment 90. The first rod segment 80 includes a cylindrical portion 82 and a semi-cylindrical portion 84. The cylindrical portion 82 may be integral with or otherwise connected to a dynamic central portion, such as the dynamic central portions shown in FIG. 4B. However, the cylindrical portion 82 of FIGS. 6A and 6B need not be connected to a dynamic portion, and may also be connected to a rigid length of rod. The semi-cylindrical portion 84 includes a flat surface 88 and a longitudinal slot 84. The longitudinal slot is provided in the central portion of the flat surface 88.

The second rod segment 90 also includes a cylindrical portion 92 and a semi-cylindrical portion 94. The cylindrical portion 92 may be integral with or otherwise connected to a dynamic central portion, such as the dynamic central portions shown in FIG. 4B. However, the cylindrical portion 92 of FIGS. 6A and 6B need not be connected to a dynamic portion, and may also be connected to a rigid length of rod. The semi-cylindrical portion 94 of the second rod segment 90 includes a flat surface 98 and a post 96 extending through the flat surface 98. In the embodiment of FIGS. 6A and 6B, the post 96 is provided as a bolt secured within a hole 99 in the semi-cylindrical portion 94 of the second rod segment 90. The bolt includes a head 97 and a threaded shaft (not shown). In this embodiment, the bolt 96 threadedly engages the hole 99 and the bolt head 97 rests within the slot 86. However, the post may be provided on the rod segment in numerous other ways, as will be recognized by those of skill in the art. For example, the post 96 may alternatively be integrally formed on the flat surface 98 of the semi-cylindrical portion 94 and the head 97 may be swaged or retained by other means to prevent disassembly of the two rod components 84 and 94.

As shown in FIGS. 6A and 6B, the flat surface 88 of the first rod segment 80 is configured to engage the flat surface 98 of the second rod segment 90 with the post 96 of the second rod segment extending into the slot 86 of the first rod segment. With this arrangement, the first rod segment 80 is adjustable relative to the second rod segment 90, with the first rod segment 80 in a slideable relationship with the second rod segment 90. In particular, the post 96 is configured to slide within the slot 86 with the flat surface 88 of the first segment 80 engaging the flat surface 98 of the second segment 90. When the first rod segment 80 is adjusted to a desired position, the first rod segment may be locked relative to the second rod segment. In the embodiment of FIGS. 6A and 6B, this is accomplished by tightening the bolt 96 within the threaded cavity 99 such that the head 97 of the bolt is compressed against a surface in the slot, thus forcing the first flat surface 88 into further engagement with the second flat surface 98 and locking the first rod segment 80 relative to the second rod segment.

Figure 7A:
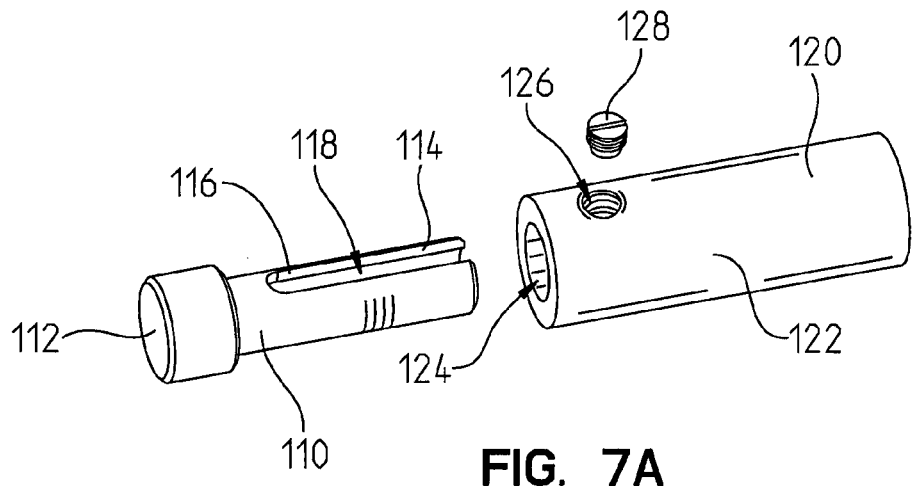
FIG. 7A shows a perspective view of another exemplary embodiment of an adjustable rod configured for use with the spine stabilization system of FIG. 1.
Figure 7B:
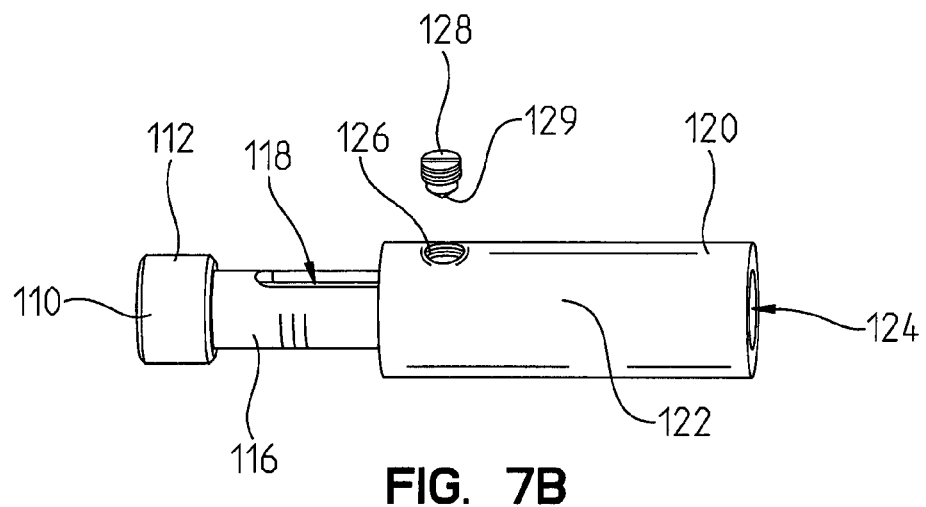
FIG. 7B shows a perspective view of the rod of FIG. 7A with a first rod segment inserted into a second rod segment.
Figure 7C:
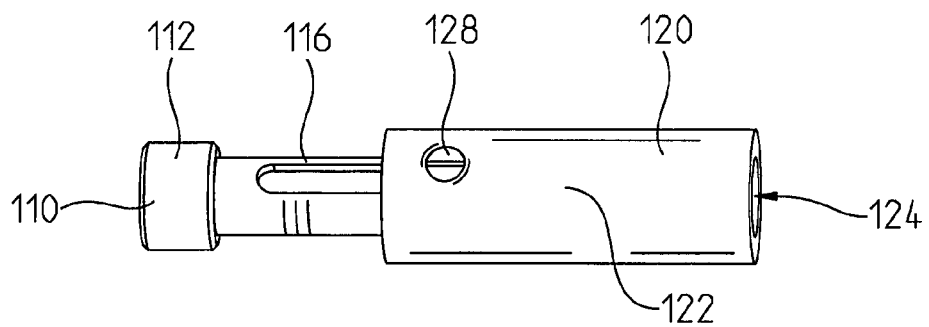
FIG. 7C shows a perspective view of the rod of FIG. 7A with the first rod segment fixed to the second rod segment.

FIGS. 7A-7C show an alternative embodiment of two adjustable rod segments 110 and 120. The first rod segment 110 includes a cylindrical portion 112 with a junction portion comprising a fork 114 formed on the end of the cylindrical portion 112. The fork includes two fingers 116 with a slot 118 provided between the fingers 116.

The second rod segment 120 includes a cylindrical portion 122 including a tube portion providing an axial channel 124 and a threaded screw hole 126. The axial channel 124 is configured to receive the fingers 116 of the first rod segment 110. A set screw 128 with a tapered tip 129 is configured to threadedly engage the screw hole 126.

When the fingers 116 of the first rod segment 110 are inserted into the axial channel 124 of the second rod segment 120, the first rod 110 segment slideably engages the second rod segment 120. Once the first rod segment 110 is positioned in a desired location relative to the second rod segment 120, the slot 118 is aligned with the screw hole 126, and the set screw 128 is placed into the screw hole 126 and rotated. As the screw 128 is rotated, the tapered tip 129 enters the slot 118 until the conical sides of the tapered tip engage the sides of the slot, thus locking the first rod segment 110 relative to the second rod segment 120.

Figure 8A:
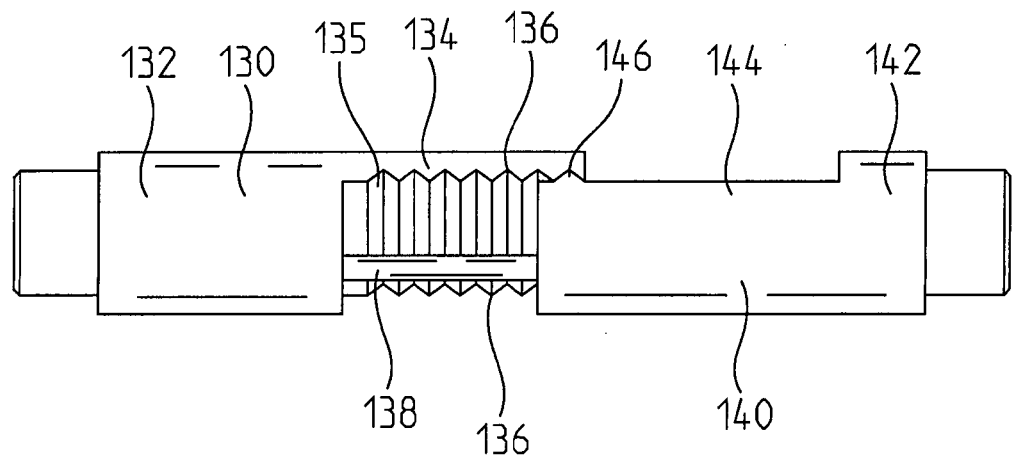
FIG. 8A shows a perspective view of yet another exemplary embodiment of an adjustable rod configured for use with the spine stabilization system of FIG. 1.
Figure 8B:
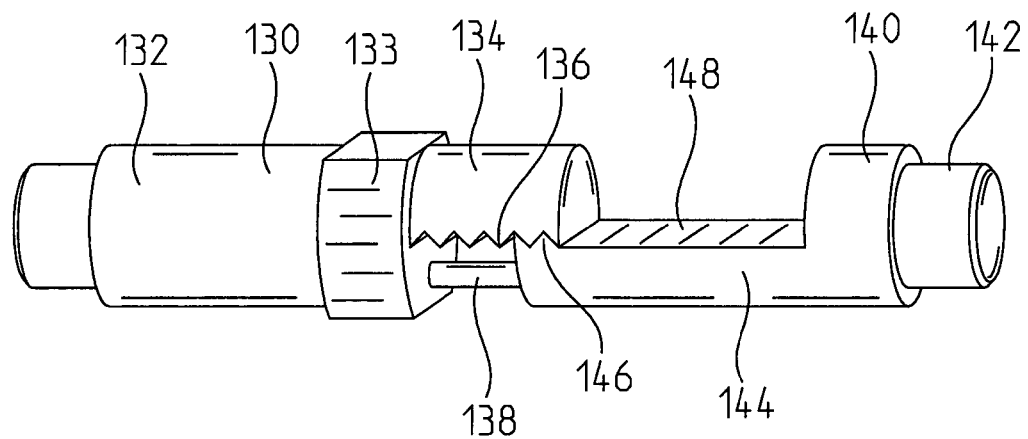
FIG. 8B shows a perspective view of an alternative embodiment of the rod of FIG. 8A.

With reference now to FIGS. 8A and 8B, another alternative embodiment of two adjustable rod segments 130, 140 in a slideable relationship is shown. In this embodiment, the first rod segment 130 includes a cylindrical portion 132 and a semi-cylindrical portion 134. The semi-cylindrical portion 134 includes a plurality of teeth 136 positioned along an inner surface 135 of the semi-cylindrical portion. A guide post 138 extends from the end of the cylindrical portion 132 such that it is traverses the space provided along the inner surface 135 of the semi-cylindrical portion 134 where the teeth 136 are located.

The second rod segment 140 also includes a cylindrical portion 142 and a semi-cylindrical portion 144. The semi-cylindrical portion includes a flat surface 148 with at least one tooth 146 provided on the flat surface 148. The tooth 146 on the second rod segment 140 is configured to engage the plurality of teeth 136 on the first rod segment 130. The semi-cylindrical portion 144 of the second rod segment 140 also includes a channel configured to receive the guide post 138 extending from the first cylindrical portion. With the guide post 138 of the first rod segment 130 extending into the channel of the second rod segment 140, the first rod segment 130 is slideably connected to the second rod segment 140, with the inner surface 135 of the first rod segment engaging the flat surface 148 of the second rod segment. As the first rod segment 130 slides relative to second rod segment 140, the tooth 146 engages successive grooves between the plurality of teeth 136 of the first rod segment 130. This successive engagement of teeth temporarily locks the first rod segment 130 in place relative to the second rod segment 140. By providing sufficient opposing forces between the first rod segment 130 and the second rod segment, the teeth are forced into successive engagement positions. Once the desired position of the first rod segment 130 relative to the second rod segment 140 is achieved, the opposing forces are removed from the rod segments 130, 140 and the rod segments remain locked in place until sufficient opposing forced dislodge the locking teeth 136, 146.

One of skill in the art will recognize that various alternative embodiments of the arrangement of FIGS. 8A and 8B are possible. For example, FIG. 8B shows a slightly different arrangement than that of FIG. 8A, where a flared portion 133 is provided between the cylindrical portion 132 and the semi-cylindrical portion 134. Also, in the embodiment of FIG. 8B, the semi-cylindrical portion 134 is shorter and includes fewer teeth 136 than the embodiment of FIG. 8A. Of course, numerous other alternative embodiments are possible.

Figure 9A:
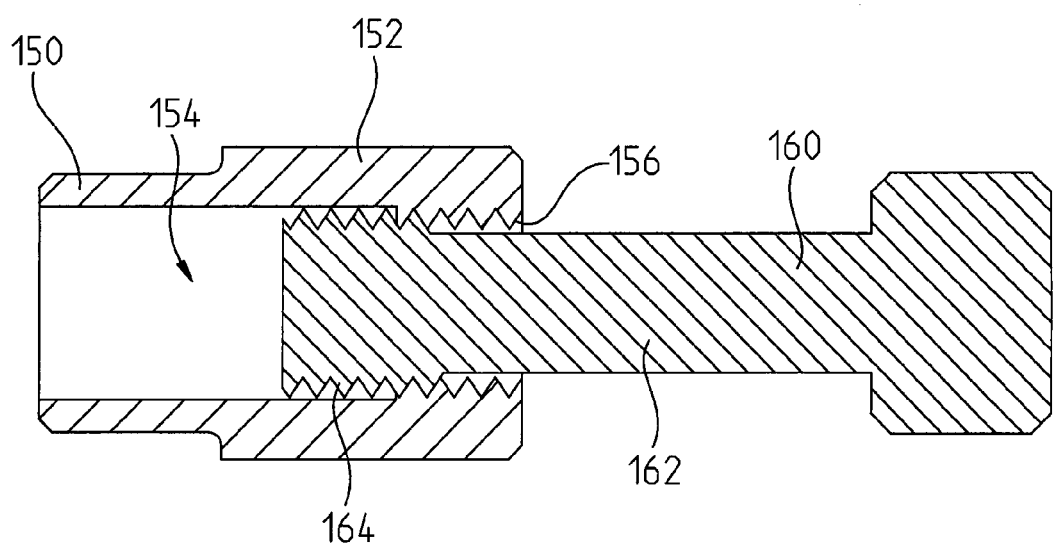
FIG. 9A shows a cross-sectional view of another exemplary embodiment of an adjustable rod configured for use with the spine stabilization system of FIG. 1.

FIG. 9A shows another alternative embodiment of a connection mechanism for two rod segments 150 and 160, where the first rod segment 150 is adjustable relative to the second rod segment 160. In this arrangement, a first rod segment 150 comprises a cylindrical portion 152 with an associated cylindrical cavity 154. The interior of the cylindrical portion 152 is threaded near a mouth 156 to the cylindrical cavity 154. The second rod segment 160 includes a cylindrical portion 162 configured to fit within the cylindrical cavity 154 of the first rod segment 150. The end 164 of the second rod segment 140 is threaded on an exterior surface, and threadedly engages the mouth 156 of the first rod segment 150. Accordingly, when the first rod segment 150 is rotated past the threads at the mouth 156 of the second rod segment 160, the position of the first rod segment 150 is adjustable relative to the second rod segment 160. A locking means (not shown), such as a set screw provided in a hole in the first rod segment 160, may be provided to lock the first rod segment 150 in place relative to the second rod segment 160.

In each embodiment of FIGS. 6A-9A various potential locking means are discussed for locking the first rod segment in place relative to the second rod segment. However, numerous other options are available for locking rod segments in place. Examples of such locking methods include the following: deflection of tabs on a male post to create a friction lock with a female tube; other friction locks such as press-fit or other deflectable mechanisms; bonding means such as adhesives, clamps, cold welds, swage locks, collets, and smart metal alloys (also referred to as memory metals) such as nickel-titanium (NiTi) which exhibit temperature dependent memory properties wherein the segments are comprised of memory metal components which expand or contract when placed in the body.

Figure 9B:
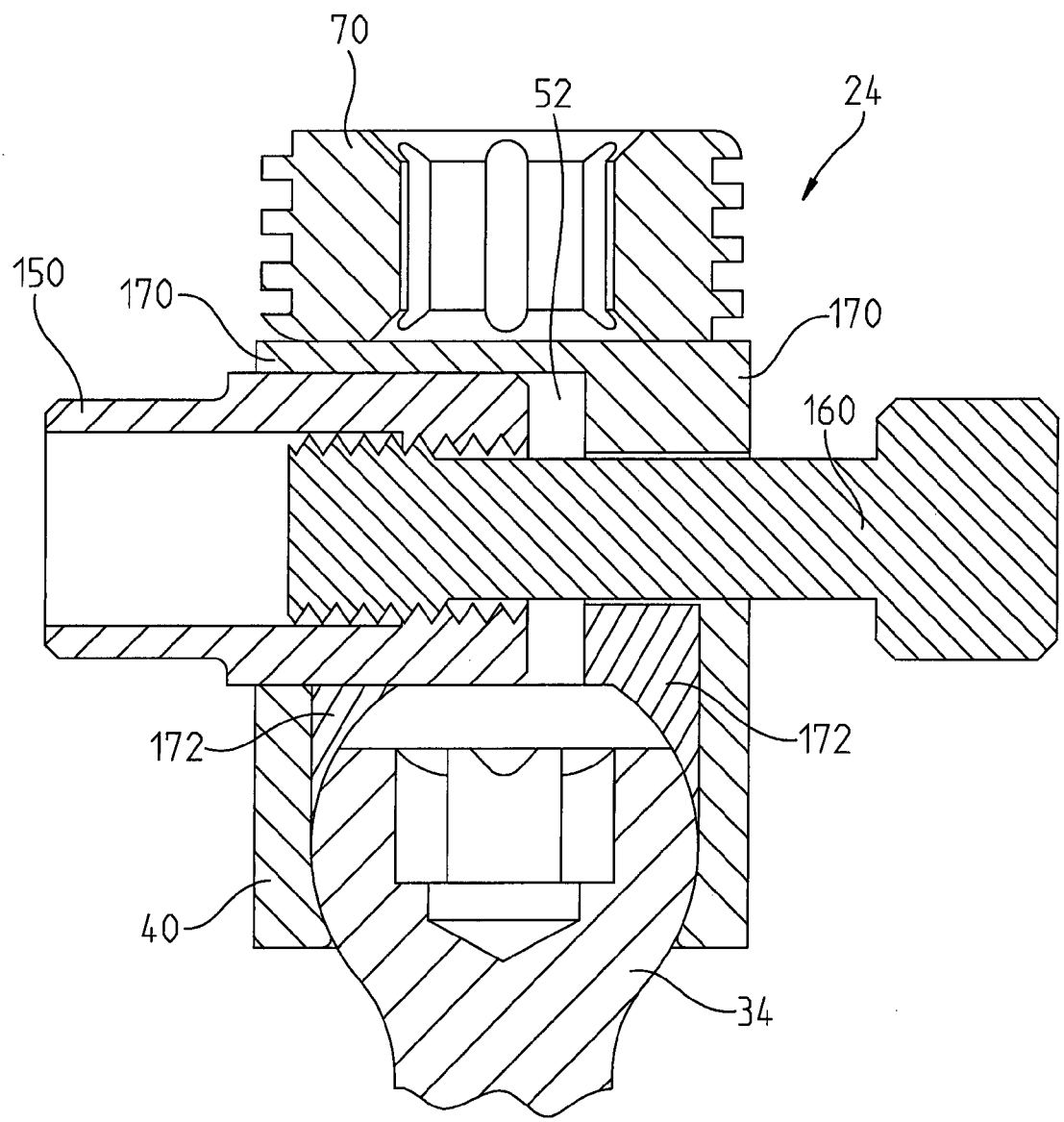
FIG. 9B shows a cross-sectional view of the adjustable rod of FIG. 9A secured within a bone anchor.

One exemplary alternative means for locking rod segments in place is shown in FIG. 9B. In this embodiment, the first rod segment 150 is locked in place relative to the second rod segment 160 by virtue of their placement within the rod cavity 52 of the bone anchor 24. The rod segments 150 and 160 engage each other in the rod cavity in an overlapping fashion. As shown in FIG. 9B, multiple bearing components are placed within the bone anchor 24 to support the rod. In particular, the bearing components comprise an upper bearing 170 and a lower bearing 172. The upper bearing 170 and lower bearing 172 are both stepped, thus creating a rod cavity 52 having two different diameters. The first diameter is dimensioned to receive the first rod segment 150. The second diameter is dimensioned to receive the second rod segment 160. The upper bearing 170 and lower bearing 172 may be comprised of a compressible material such as UHMWPE. When the set screw 70 is tightened within the bone anchor 24, the upper bearing 172 is compressed against the rod segments 150 and 160, thus locking the rod segments in place within the bone anchor 24.

While only the rod segments 150, 160 from the embodiment of FIG. 9A are shown as being locked by the arrangement of FIG. 9B, it will be appreciated by those of skill in the art that any of the rod segments from the embodiments of FIGS. 6A-8B may also be locked by a similar arrangement where the ends of the rod segments are positioned within the rod cavity 52 of the bone anchor 24. Furthermore, one of skill in the art will recognize that numerous other arrangements may be provided where two rod segment ends are positioned within and secured to the bone anchor 24, thus locking the respective rod segments relative to one another.

Figure 10:
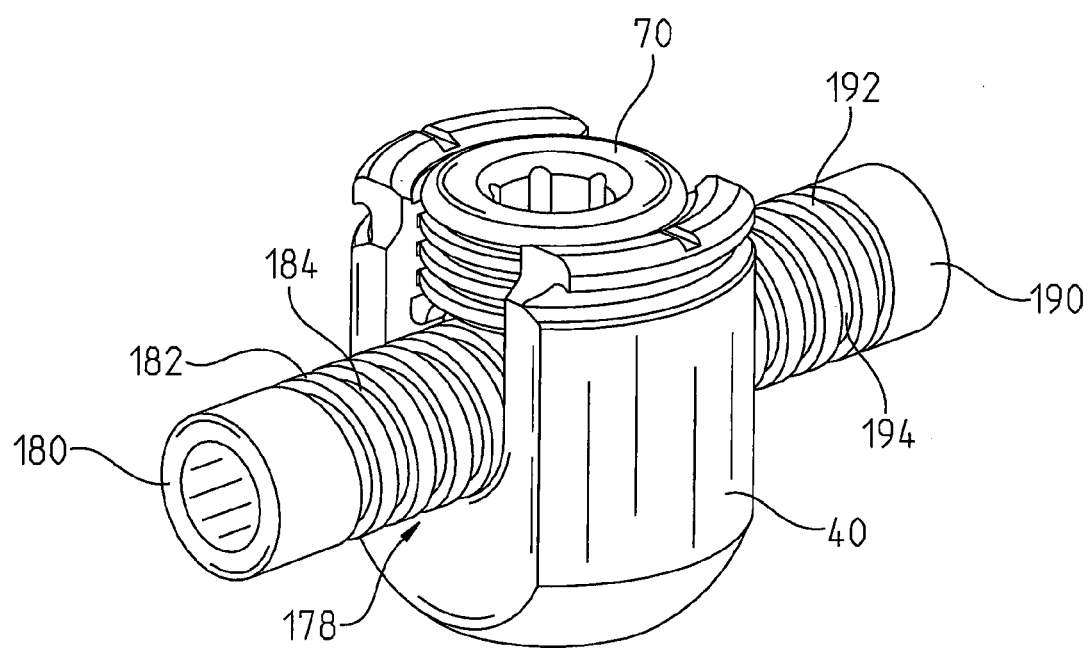
FIG. 10 shows a perspective view of yet another alternative embodiment of an adjustable rod configured for use with the spine stabilization system of FIG. 1 and positioned within a bone anchor.

FIG. 10 shows an alternative embodiment of an arrangement where two rod segments are positioned within and secured to the bone anchor 24, thus locking the respective rod segments relative to one another within the bone anchor 24. In the embodiment of FIG. 10, a first rod segment 180 includes a plurality of ribs 182 and associated grooves 184 positioned on the end of the rod segment. Similarly, the second rod segment 190 includes a plurality of ribs 192 and associated grooves 194.

In order to lock the first rod segment 180 relative to the second rod segment 190, the rod segments are slid within the rod cavity of the holding member such that they provide a desired length. When the rod segments are at the desired length, the grooves 184, 194 of the rod segments are configured to ride within the bottom portion of a U-shaped saddle 178 provided in the holding member 40. In particular, when one of the grooves 184 of the first rod segment 180 engages the bottom portion of the saddle 178, the ribs 182 of the first rod segment 180 are positioned on the sides of the saddle, with one rib on the exterior of the holding member and an adjacent rib on the interior of the holding member. The second rod segment engages the saddle on the opposite side of the holding member 40 in a similar fashion. When the set screw is tightened, the rod is forced downward against the saddle 178, and the ribs 182, 192 lock the first rod segment 180 and second rod segment 190 in place within the holding member 40.

When the rod segments 180, 190 of FIG. 10 are secured within the bone anchor, the rod segments 180, 190 may be arranged in various arrangements. For example, the rod segments may overlap one another, may abut one another, or may be completely removed from one another. Ultimately, the relationship of the rod segments 180, 190 within the bone anchor 24 depends on the configuration of the rod segments and their required position within the bone anchor in order to provide an appropriately sized rod.

As described above, FIGS. 6A-10 show various embodiments where rod segments are adjustable with respect to one another. As already noted herein, one of skill in the art will recognize that various adaptations and different embodiments are possible. For example, the adjustable rod segments could be provided by numerous other means, such as a ball and socket design where the ball slides within an elongated socket. Another example is an accordion-like rod member with a plurality of expanding or contracting connected diamond shaped members. In one such embodiment, adjustment of the length of the rod segment could be through a gear. Therefore, although the present invention has been described with respect to certain preferred embodiments, it will be appreciated by those of skill in the art that other implementations and adaptations are possible without departing from the scope of the invention.

Rod Segments of Discrete Sizes

With reference now to FIGS. 11A-12B, alternative embodiments of a modular multi-level PDS system are shown. In these embodiments, adjustments may be made to the distance between bone anchors by using rod segments of discrete lengths. In this embodiment, when a surgeon determines a desired distance between two bone anchors the surgeon simply chooses a rod segment of an appropriate length and joins the rod segment to existing rod segments within the PDS assembly. Accordingly, the rod segments should be constructed in a manner that allows them to be easily joined to other rod segments. Various examples of such rod segments configured to easily connect to adjacent rod segments are provided in FIGS. 11A-12B.

Figure 11A:
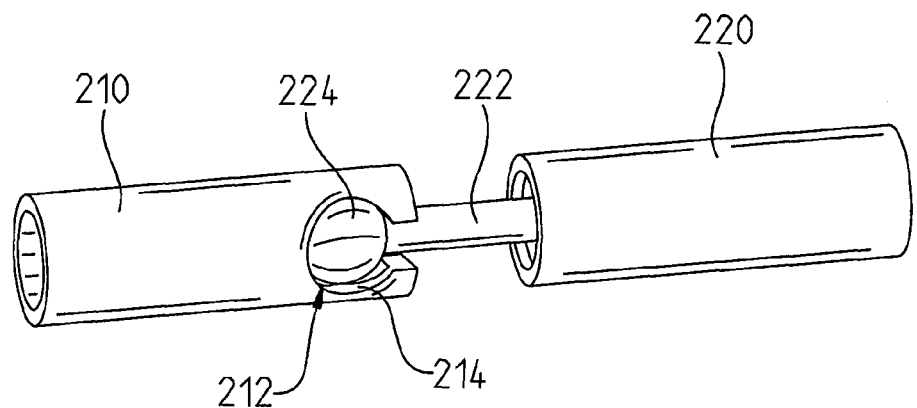
FIG. 11A shows a perspective view of a connection arrangement between a first rod segment and a second rod segment configured for use with the spine stabilization system of FIG. 1.
Figure 11B:
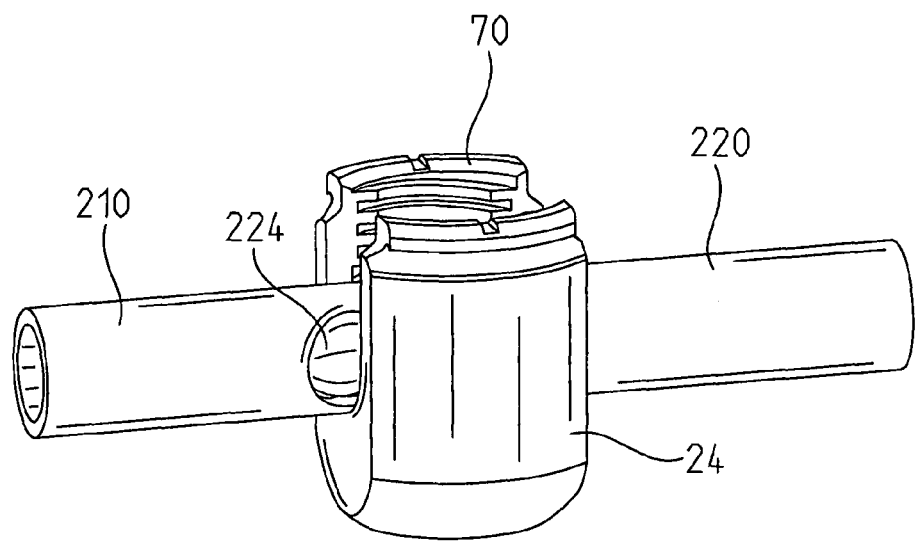
FIG. 11B shows a perspective view of the rod segments of FIG. 11A positioned within a bone anchor.

FIG. 11A shows a first rod segment 210 connected to a second rod segment 220. The first rod segment includes a socket 212 with a side door 214. The second rod segment includes a post 222 with a ball 224 attached to the end of the post. The ball 224 is designed and dimensioned to fit within the socket 212. To assemble the two rod segments, the ball 224 of the second rod segment 220 is slid through the side door 214 of the first rod segment 210. After the first rod segment 210 is joined to the second rod segment 220, the two rod segments are placed into the holding member 40 of a bone anchor, as shown in FIG. 11B. When a set screw is tightened within the bone anchor, the two rod segments 210 and 220 are secured to the holding member. With this arrangement, various discretely sized rod segments may be provided, allowing the surgeon to select an appropriate size for a particular connection in a PDS assembly. If a dynamic portion is provided on the rod segment, it may be conveniently positioned on the rod segment during manufacturing such that it will be centered between bone anchors when used in a PDS assembly.

Figure 12A:
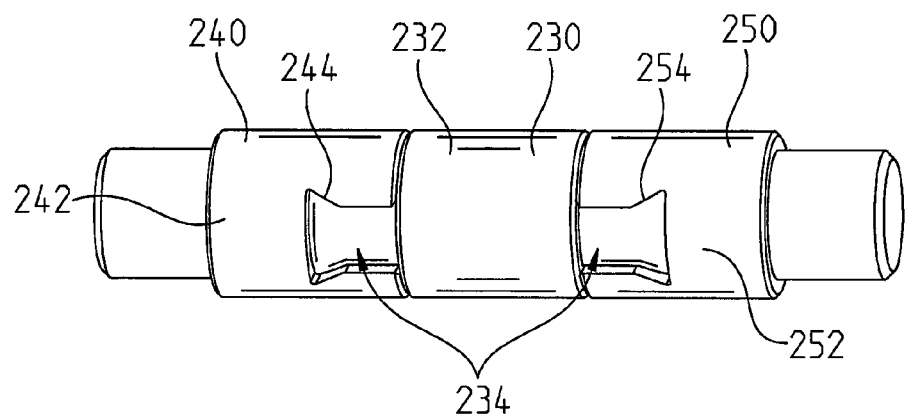
FIG. 12A shows a perspective view of another connection arrangement between a first rod segment and a second rod segment configured for use with the spine stabilization system of FIG. 1.

With reference now to FIG. 12A, three distinct rod segments are shown. In this arrangement rod segments of different discrete lengths are connected together using a mortise and tenon arrangement. One rod segment 230 acts as a connector for rod segments adjacent to the connector. The connector rod segment 230 includes a cylindrical portion 232 with two dovetail shaped tenons 234 extending from the ends of the cylindrical portion 232. A second rod segment 240 includes a cylindrical portion 242 with a mortise 244 formed in the end of the cylindrical portion. The mortise 244 provides a cavity that is configured to receive a tenon 234 of the first rod segment 230. Similarly, the third rod segment 250 includes a cylindrical portion 252 with a mortise 254 formed in the end of the cylindrical portion. This mortise 254 is also configured to receive a tenon 234 of the first rod segment 230. If rod segments 230, 240, 250 of different discrete lengths are available, a surgeon may build a PDS system by choosing rod segments of appropriate lengths. Similar to the arrangement shown in FIG. 11B, the rod segments may be locked together by placing adjacent ends of a rod segment within a bone anchor 24 and tightening a set screw 70 over the rod segments, thus pinning the rod segments to the bone anchor, and locking the rod segments in place relative to one another.

Figure 12B:
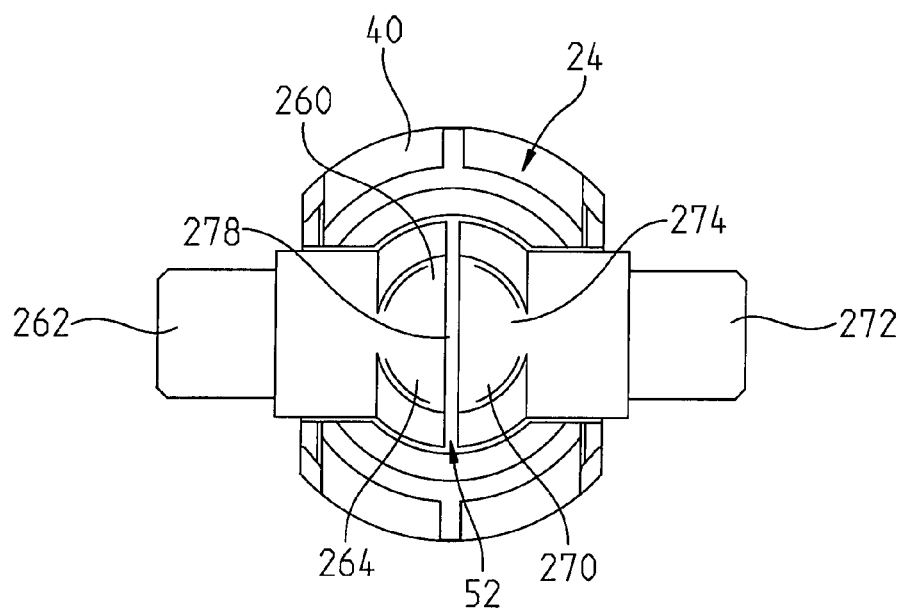
FIG. 12B shows a top view of an alternative embodiment of the mortise and tenon connection arrangement of FIG. 12A wherein a first rod segment and a second rod segment are secured within a bone anchor.

FIG. 12B shows an alternative embodiment of a mortise and tenon connection arrangement for rod segments. In the embodiment of FIG. 12B, the ends of two rod segments are shown positioned within the rod cavity of a bone anchor. A first rod segment 260 comprises a cylindrical portion 262 with a dovetail shaped tenon 264 connected to the end of the cylindrical portion 262. The second rod segment 270 also comprises a cylindrical portion 272 with a dovetail shaped tenon 274 connected to the end of the cylindrical portion 272. The two tenons 264 and 274 are configured to fit within the rod cavity 52 in the holding member 40 of the bone anchor 24. Both of the tenons 264, 274 include a flat top configured to engage a set screw (not shown) threadedly connected to the holding member 40. When the set screw is tightened in the holding member 40, the ends of the rod segments 260, 270 are compressed against a bearing member provided under the rod segments, thus locking the rod segments in place. As shown in FIG. 12B, the tenons 264 and 274 may be separated by a gap within the rod cavity 52 of the bone anchor 24 with a compressible member positioned in between. Alternatively, the tenons 264 and 274 may abut one another within the rod cavity 52.

Figure 12C:
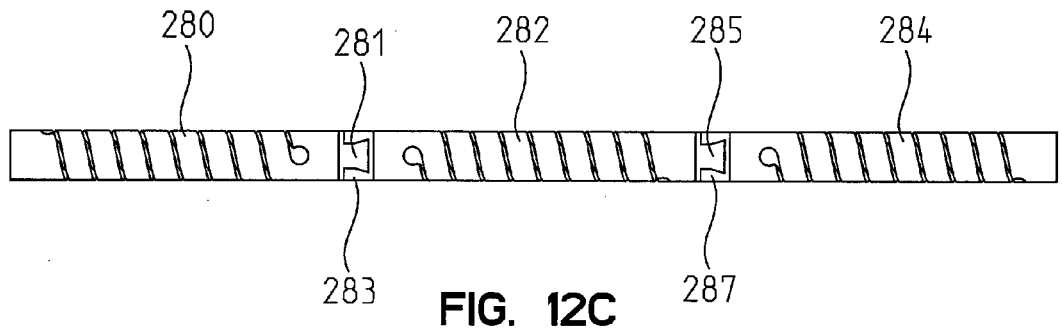
FIG. 12C shows a top view of a rod with three rod segments connected together using a mortise and tennon connection arrangement.
Figure 12D:
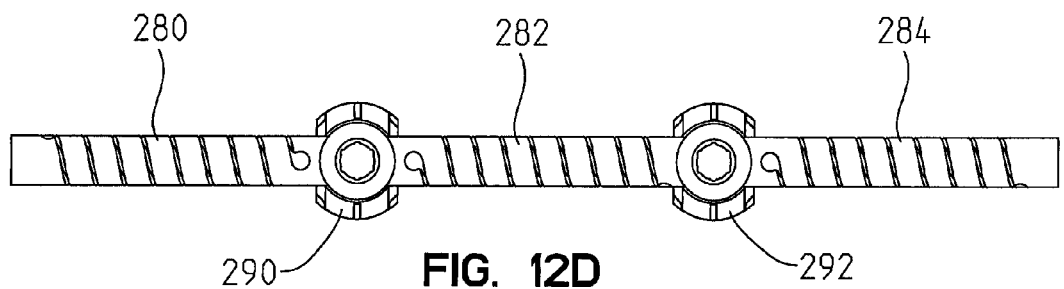
FIG. 12D shows a top view of the rod of FIG. 12C secured to bone anchors.
Figure 12E:
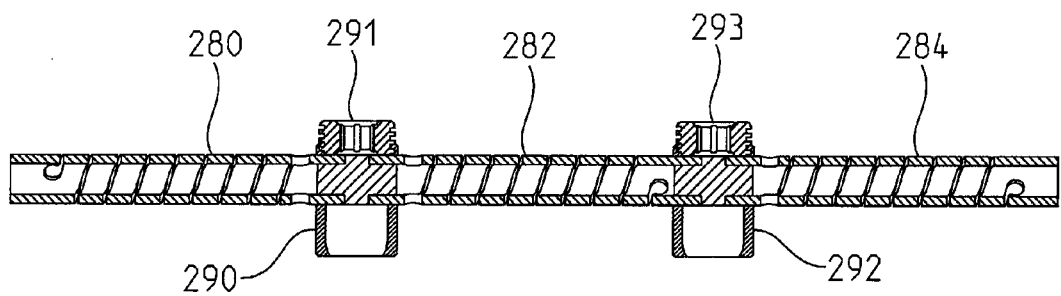
FIG. 12E shows a cross-sectional view of the rod and bone anchors of FIG. 12D.
Figure 12F:
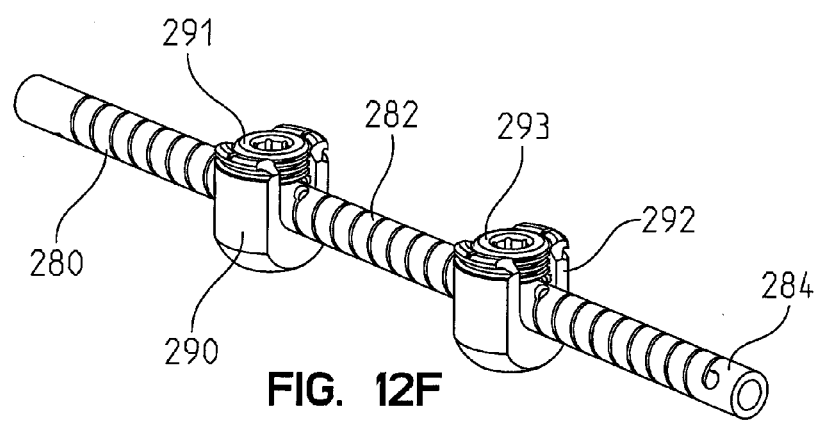
FIG. 12F shows a perspective view of the rod and bone anchors of FIG. 12D.

FIGS. 12C-F show yet another alternative embodiment of a mortise and tenon connection arrangement for rod segments. As shown in FIG. 12C, either a mortise or a tennon is formed on the end of each rod segment that connects to another rod segment. For example, rod 280 includes a mortise 281 extending from the end connected to the tennon 283 of rod segment 282. A mortise 285 is formed on the opposite end of rod segment 282 that fits within tennon 287 of rod segment 284. The mortise and tennon components on the ends of the rod segments may be integral with the rod segments, or may be attached in some fashion. For example, the mortise or tennon component may fit within the end of the rod segment with a friction fit and a set screw may be used to assist in securing the mortise or tennon component to the rod segment. As shown in FIG. 12E, the ends of the rod segments, including the mortise and tennon components, are secured to a bone anchors 290, 292. In particular, the mortise and tennon components are placed in the cavity of one of the bone anchors 290, 292 and the set screw 291, 293 of the bone anchor is tightened to secure the rod segments 280, 282, 284 to the bone anchor 290, 292. In order to accommodate segmental units of different sizes with this arrangement, the surgeon may choose different discretely sized rod segments that properly space the bone anchors 290, 292 between the patient's vertebrae.

Figure 13A:
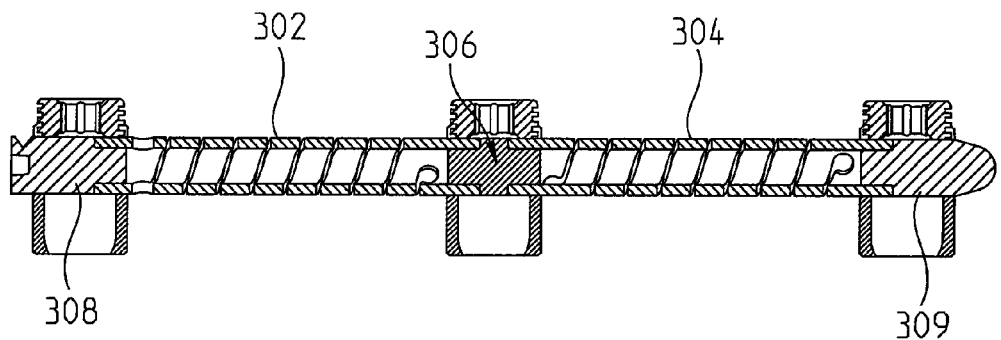
FIG. 13A shows a cross-sectional view of an alternative embodiment of a rod and bone anchors.
Figure 13B:
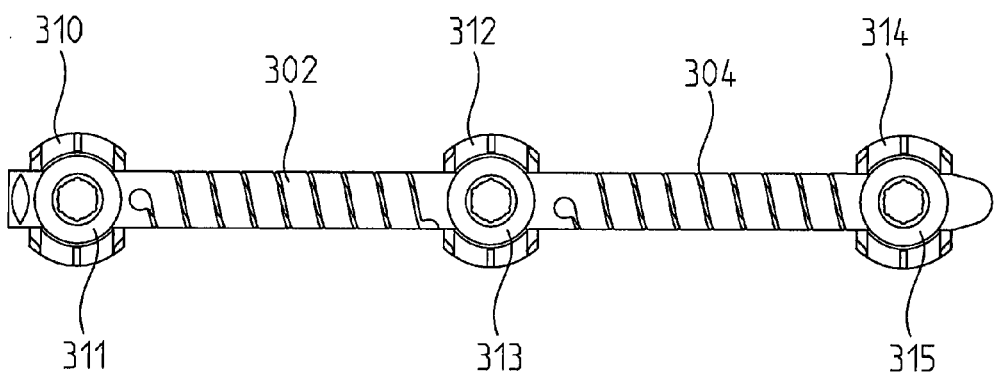
FIG. 13B shows a top view of the embodiment of FIG. 13A.
Figure 13C:
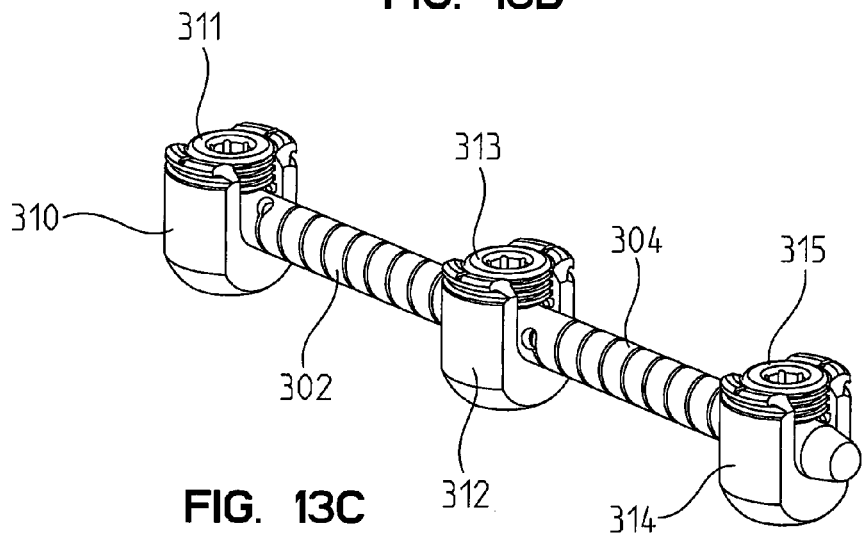
FIG. 13C shows a perspective view of the rod and bone anchors of FIG. 13A.

FIGS. 13A-13C show yet another alternative embodiment of a means for connecting rod segments. In FIG. 13A, two different rod segments 302, 304 are shown. A connector segment 306 is placed between each rod segment 302, 304. The connector segment 306 acts to join the two segments 302, 304, similar to the arrangement of FIG. 12A. However, unlike FIG. 12A, the connector segment 306 in this embodiment includes opposing threaded posts configured to threadedly engage the interior cylindrical walls of the adjacent segments 302, 304. End plugs 308, 309 are provided to threadedly engage the ends of rod segments that are not connected to other rod segments. The connector segment 306 and end plugs 308, 309 are designed to be secured within one of the bone anchors 310, 312, 314. In particular, the connector 306 and end plugs 308, 309 are placed in the cavities one the bone anchors 310, 312, 314, and the set screws 311, 313, 315 are tightened to secure the rod segments 302, 304 to the bone anchors 310, 312, 314. In order to accommodate segmental units of different sizes with this arrangement, the surgeon may choose different discretely sized rod segments 302, 304 or connectors 306 that properly space the bone anchors 310, 312, 314 between the patient's vertebrae.

Figure 14C:
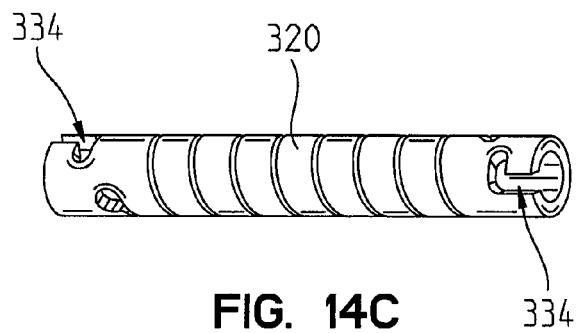
FIG. 14C shows a perspective view of a rod segment of FIG. 14A.

FIGS. 14A-14F show another embodiment, of a connection arrangement between two rod segments 320, 322 and a third segment in the form of a joining component 337. As shown in FIG. 14A, the two rod segments 320 and 322 are positioned between three bone anchors 324, 326, 328, with a joining component 337 retained with each bone anchor. In this arrangement, at least one pin 332 extends outward from the joining component 337, and a groove 334 in the end of a rod segment is configured to receive the pin 332 of the joining component 337.

Figure 14D:
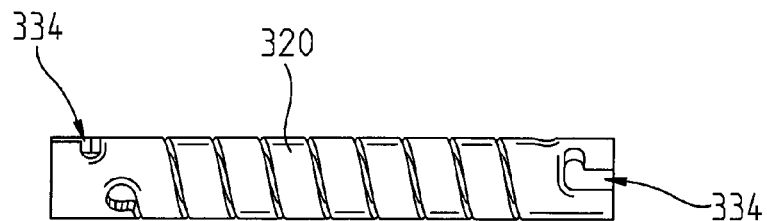
FIG. 14D shows a side view of the rod segment of FIG. 14C.

An exemplary rod segment 320 with end grooves 334 is shown in FIGS. 14C and 14D. The groove 334 is cut in the end of the rod segment 320, cutting axially into the exterior wall of the rod starting at the mouth, and then turning radially around the exterior wall. The groove 334 generally extends from approximately 20 to 300 degrees around the rod segment. In one embodiment, the groove 334 advantageously extends from 30 to 60 degrees around the rod segment.

Figure 14E:
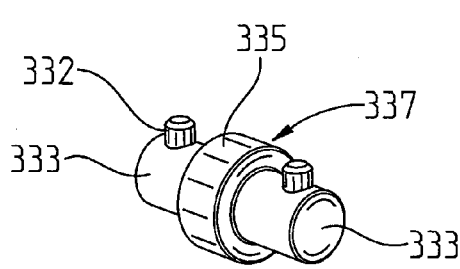
FIG. 14E shows a perspective view of a joining component of FIG. 14A.
Figure 14F:
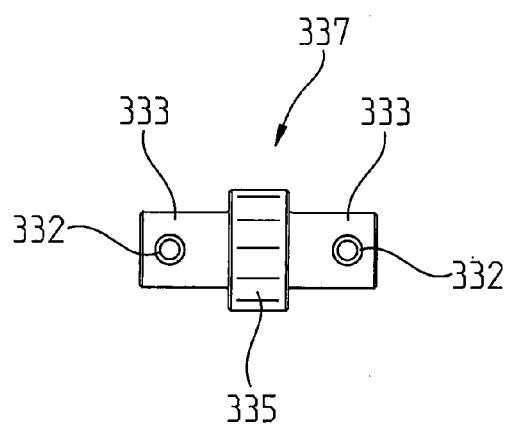
FIG. 14F shows a top view of the joining component of FIG. 14E.

An exemplary joining component 337 is shown in FIGS. 14E and 14F. The joining component 337 is configured to fit within the rod cavity of a bone anchor. The joining component 337 includes a main body 335 that substantially conforms to the shape of the other rod segments. This main body 335 is designed and dimensioned to be secured within the rod cavity of a bone anchor. Extending from the main body is at least one axial stub 333. A pin 332 extends radially from the stub 333. Although the embodiment of FIGS. 14E and 14F show two stubs 333, other joining components 337 may include only a single stub, such as those shown in the bone anchors 324 and 328 of FIG. 14A. The joining components 337 with only one stub 333 are generally designed to terminate the rod assembly at the bone anchor by receiving only one rod segment on one side of the bone anchor.

As shown in the diagram of FIG. 14B, in order to assembly a rod segment 322 and a joining component 337, the pin 332 of the joining component 337 is inserted into the groove 334 of the rod segment 322. Following the path of travel 335 formed by the groove 334, the pin travels to where the groove terminates. This locks the rod segment 322 to the joining member 337. Of course, the amount of rotation required to lock the rod segments 320 and 322 together via the joining member 337 is dependent upon the length of the groove 334. Once the rod segments 320, 322 are assembled with the joining components 337, the joining components 337 are placed into the cavities 330 of the bone anchors 324, 326, 328, and the complete PDS assembly may be fixed to the vertebrae.

The various PDS components disclosed herein may be sold and marketed in various fashions. In one embodiment, the PDS components are marketed and sold as a surgical kit. For example, the kit may comprise a plurality of rod segments and a plurality of bone anchors that may be used to mount the rod segments to the vertebrae and build a complete PDS system. The surgeon uses an instrument, such as calipers, to measure the distance between adjacent vertebrae to which the bone anchors will be attached. With the measured distance between adjacent vertebrae, appropriately sized rod segments may be chosen to extend between the holding members. The act of choosing appropriately sized rod segments may involve choosing various rod segments of different lengths or adjusting the adjustable rod segments disclosed herein to appropriate lengths. After preparing rod segments having lengths that match the distance between the vertebrae, the PDS system may be assembled.

Accordingly, a method is disclosed herein for constructing a multi-level spine stabilization system. The method comprises, providing a plurality of securing members and a plurality of rod segments configured to extend between the plurality of securing members. Each of the plurality of securing members is configured for attachment to the bone. The method further comprises measuring the distances between a plurality of adjacent vertebrae in a patient. After these measurements are taken, rod segments of an appropriate length are selected or two coupled rod segments are adjusted relative to one another to provide a rod segment that spans the appropriate length between two adjacent securing members fixed to two adjacent vertebrae. By repeating the method for a plurality of adjacent vertebrae, a multi-level spine stabilization system is constructed.

Although the present invention has been described with respect to certain preferred embodiments, it will be appreciated by those of skill in the art that other implementations and adaptations are possible without departing from the scope of the invention. Several examples of such alternative embodiments are provided above. Moreover, there are advantages to individual advancements described herein that may be obtained without incorporating other aspects described above. Therefore, the spirit and scope of the appended claims should not be limited to the description of the preferred embodiments contained herein.

What is claimed is:

1. A spine stabilization system, comprising:
a bone anchor including a holding member defining an interior space;
a first spinal rod segment having a first end portion positioned in said interior space; and
a second spinal rod segment having a second end portion positioned in said interior space, wherein said first end portion of said first spinal rod is spaced apart from said second end portion of said second spinal rod such that said first spinal rod segment does not contact said second spinal rod segment in said interior space,
wherein said bone anchor further includes a set screw,
wherein when said set screw is located within said interior space of said holding member, said set screw contacts both (i) said first end portion of said first spinal rod, and (ii) said second end portion of said second spinal rod.

2. The spine stabilization system of claim 1, wherein:
said bone anchor further includes a bearing member located within said interior space of said holding member, and
said bearing member contacts both (i) said first end portion of said first spinal rod, and (ii) said second end portion of said second spinal rod.

3. A spine stabilization system, comprising:
a bone anchor including a holding member having a pair of arms defining an interior space;
a first spinal rod segment having a first end portion positioned in said interior space; and
a second spinal rod segment having a second end portion positioned in said interior space, wherein said first end portion of said first spinal rod is spaced apart from said second end portion of said second spinal rod such that said first spinal rod segment does not contact said second spinal rod segment in said interior space,
wherein each of said first end portion of said first spinal rod and said second end portion of said second spinal rod includes one of a tenon and a mortise positioned within said interior space of said holding member,
wherein said first end portion of said first spinal rod includes a first tenon positioned within said interior space of said holding member, and
wherein said second end portion of said second spinal rod includes a second tenon positioned within said interior space of said holding member.

4. The spine stabilization system of claim 3, wherein:
said holding member includes an interior surface that defines said interior space, and
said interior surface includes a concave portion that is formed complementary to both said first tenon and said second tenon when said first end portion of said first spinal rod and said second end portion of said second spinal rod are positioned within said interior space of said holding member.

5. The spine stabilization system of claim 3, wherein:
said bone anchor further includes a set screw,
said first tenon includes a first flat top surface configured to contact said set screw, and
said second tenon includes a second flat top surface configured to contact said set screw.

6. A multi-level spine stabilization system comprising:
a securing member configured for attachment to bone, the securing member defining a unitary interior space; and
a connecting structure extending though the interior space of the securing member and secured to the securing member, the connecting structure including a first segment and a second segment, wherein the first segment and the second segment are both at least partially positioned within the securing member, and wherein the first segment is removed from the second segment of the connecting structure within the unitary interior space of the securing member,
wherein the connecting structure further includes a third segment positioned between the first segment and the second segment within the interior space of the securing member, wherein the first segment and the second segment are both connected to the third segment of the connecting structure: and wherein a set screw is positioned in the securing member and configured to retain the first segment, the second segment, and the third segment within the interior space of the securing member, and wherein the first segment of the connecting structure includes a first tenon configured to fit within the interior space of the securing member, the second segment of the connecting structure includes a second tenon configured to fit within the interior space of the securing member, and the third segment of the connecting structure includes a first mortise engaging the first tenon and a second mortise engaging the second tenon such that the first segment and the second segment are both connected to the third segment of the connecting structure with a mortise and tenon connection arrangement.

* * * * *